(12) United States Patent
Lee

(10) Patent No.: US 6,860,886 B1
(45) Date of Patent: Mar. 1, 2005

(54) RECIPROCATING SURGICAL TOOL FOR USE AT VARIABLE ANGLES AND IN MULTIPLE DIRECTIONS

(76) Inventor: Hee-Young Lee, 787-14, Samhak-dong, Kunsan, Cholrabukdo, 373-310 (KR)

( * ) Notice: Subject to any disclaimer, the term of this patent is extended or adjusted under 35 U.S.C. 154(b) by 0 days.

(21) Appl. No.: 10/049,448

(22) PCT Filed: Nov. 29, 1999

(86) PCT No.: PCT/KR99/00717

§ 371 (c)(1),
(2), (4) Date: Feb. 12, 2002

(87) PCT Pub. No.: WO01/13802

PCT Pub. Date: Mar. 1, 2001

(30) Foreign Application Priority Data

Aug. 19, 1999  (KR) ..................... 1999-0034321

(51) Int. Cl.$^7$ ............................................. A61B 17/14
(52) U.S. Cl. ....................................................... 606/82
(58) Field of Search ............................... 606/79, 82, 84, 606/85, 170, 177; 30/374, 392, 514

(56) References Cited

U.S. PATENT DOCUMENTS

| | | | | |
|---|---|---|---|---|
| 2,702,550 A | * | 2/1955 | Rowe ......................... | 606/178 |
| 3,642,002 A | | 2/1972 | Otterstrom | |
| 3,678,934 A | * | 7/1972 | Warfield et al. ............... | 606/79 |
| 4,031,763 A | * | 6/1977 | Eisenberg ...................... | 74/50 |
| 4,252,121 A | * | 2/1981 | Arnegger ...................... | 606/53 |
| 4,963,147 A | * | 10/1990 | Agee et al. ................. | 606/170 |
| 5,468,247 A | * | 11/1995 | Matthai et al. ............. | 606/178 |

FOREIGN PATENT DOCUMENTS

| | | |
|---|---|---|
| DE | 27 49875 A1 | 5/1979 |
| DE | 37 12929 A1 | 11/1988 |

* cited by examiner

*Primary Examiner*—Eduardo C. Robert
(74) *Attorney, Agent, or Firm*—Dilworth & Barrese, LLP

(57) ABSTRACT

A reciprocating saw for use in oral cavity bone cutting operations, including a handle, a neck extended from the handle, and a head case to be coupled to an end of the neck. A motor is mounted inside of the handle. A slider shaft is mounted inside of the head case to form an angle of approximately 90° with respect to the neck, and moves in a straight linear reciprocating direction along the slider shaft which is mounted. The slider and the motor are coupled by a power linkage device for converting rotational power of the motor to a straight linear reciprocating movement of slider whereby a direction of the bone cutting operation performed by a saw member or a file member attached to the slider forms an angle of approximately 90° with respect to an approach direction of the handle, and provides a significantly high efficiency in bone cutting operations since the bone cutting operation can be performed in a narrow space, while ensuring a wide field of view. In addition, an upper cut off portion of a mandible to which a conventional saw has a difficulty in approaching, can be easily approached and cut off.

13 Claims, 7 Drawing Sheets

RECIPROCATING SURGICAL TOOL FOR USE AT VARIABLE ANGLES AND IN MULTIPLE DIRECTIONS

BACKGROUND OF THE INVENTION

1. Field of the Invention

The present invention relates to a surgical saw for use in a bone cutting operation, and more particularly, to a reciprocating saw for use in cutting oral cavity bone, when an oral cavity bone cutting operation is performed by a linear reciprocation movement of the reciprocating saw blade without restriction within an approach direction.

2. Background Art

Reciprocating saws for surgical cutting operations of oral cavity bone are commonly used in plastic surgery. Since a bone cutting operation is preferably performed in a narrow space of the oral cavity, it is required to minimize the size of the reciprocating saw used therein. In addition, the optimization of bone cutting directions significantly affects the degree of difficulty, in a required limited time period, and pre-treatment for a surgical operation will also add to optimization of the procedure. However, a conventional surgical cutting saw does not provide such optimization of the surgical procedure.

As a conventional saw for surgical cutting operations, there are a sagittal saw, the saw blade of which is formed in the same direction as a handle thereof, as shown in FIG. 10, and an oscillating saw, the saw blade of which is formed to allow cuttings in a perpendicular direction with respect to a handle of the saw, as shown in FIGS. 11a and 11b even though the saw is installed the same direction as the handle thereof. The sagittal saw has a problem in that changing cutting directions is not easy and a large external cutoff portion is inevitable to ensure a certain space required for inserting a saw and cutting a bone because the approach direction of the saw is the same as the direction of cutting a bone. The oscillating saw also has a problem in that the efficiency of the cutting operation is low and determining the direction for bone cutting is extremely difficult to form a circular shape.

For example, when a protruding portion of a mandible 100 has to be removed by being cut in a circular shape, the sagittal saw has an excellent cutting force. However, as shown in FIG. 10, an additional cut-off portion 101 is required to be formed at an outer skin, which delays a recovery time period and makes the surgical operation more complicated. The oscillating saw is advantageous in that the pre-cutoff portion can be minimized by inserting the saw blade thereof after partially cutting the oral cavity (oral cavity cutoff portion 102). However, as shown in FIG. 11a, when an upper portion of the mandible is cut-off (at point p), the saw handle is caught by the oral cavity cutoff portion 102, which causes difficulty in determining directions and angles.

A typical oscillating saw is generally used when a bone cutting operation is performed in a direction of an angle different from the direction of the saw handle. However, if the angle is not perpendicular to the handle, i.e., if the angle is not 90° with respect to the handle, or a circular action is partially included, the cutoff operation is inefficient. (Referring to FIG. 11b, when the cutting operation is to be performed in x-axis direction, the efficiency of cutting operation is degraded since a circular action occurs, forming an arc at x-y surface.)

SUMMARY OF THE INVENTION

Therefore, it is an object of the present invention to allow an easy change in cutoff angle in a narrow space, minimization of a pre-cutoff portion, and enhancement in efficiency of the cutoff operation.

To accomplish the above object of the present invention, there is provided a reciprocating saw for use in a cutoff procedure for oral cavity bone, when the saw blade operation portion has a minimized size so as to allow for its effective use in a narrow space, and a saw blade or a file reciprocates linearly while maintaining a predetermined angle with respect to an approach direction, to thereby allow a free setup of bone cutting directions.

DETAILED DESCRIPTION OF THE PREFERRED EMBODIMENTS

Figure 1:
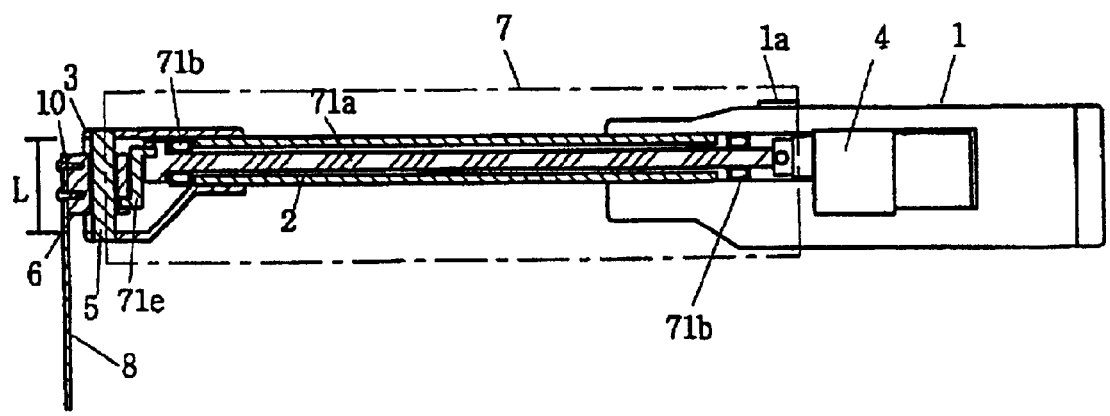
FIG. 1 is a side sectional view of a reciprocating saw according to the present invention.

A preferred embodiment of the present invention will be described hereinbelow with reference to the accompanying drawings. In the following description, like reference numerals identify similar or identical elements throughout the several views, while well-known functions or constructions are not described in detail so as not to obscure the invention in unnecessary detail.

Figure 2A:
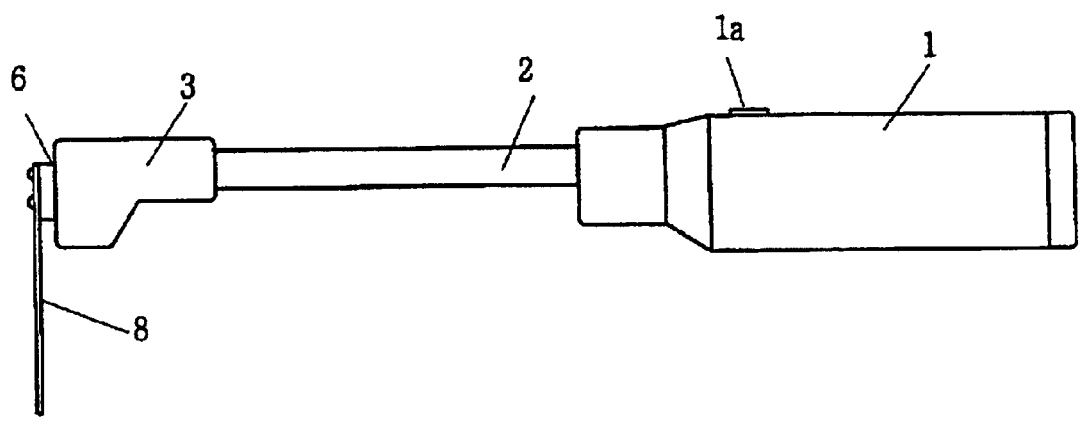
FIG. 2a is a side elevational view of the reciprocating saw shown in FIG. 1.
Figure 2B:
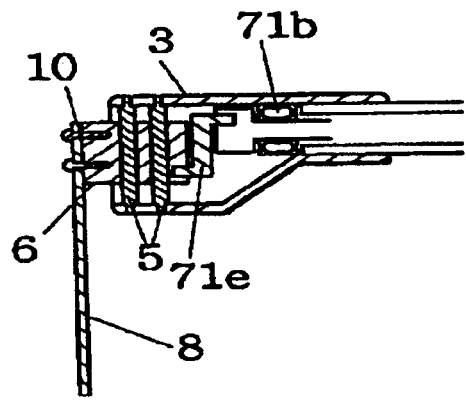
FIG. 2b is a side partial sectional view of a reciprocating saw having two slider axes according to a preferred embodiment of the present invention.
Figure 3:
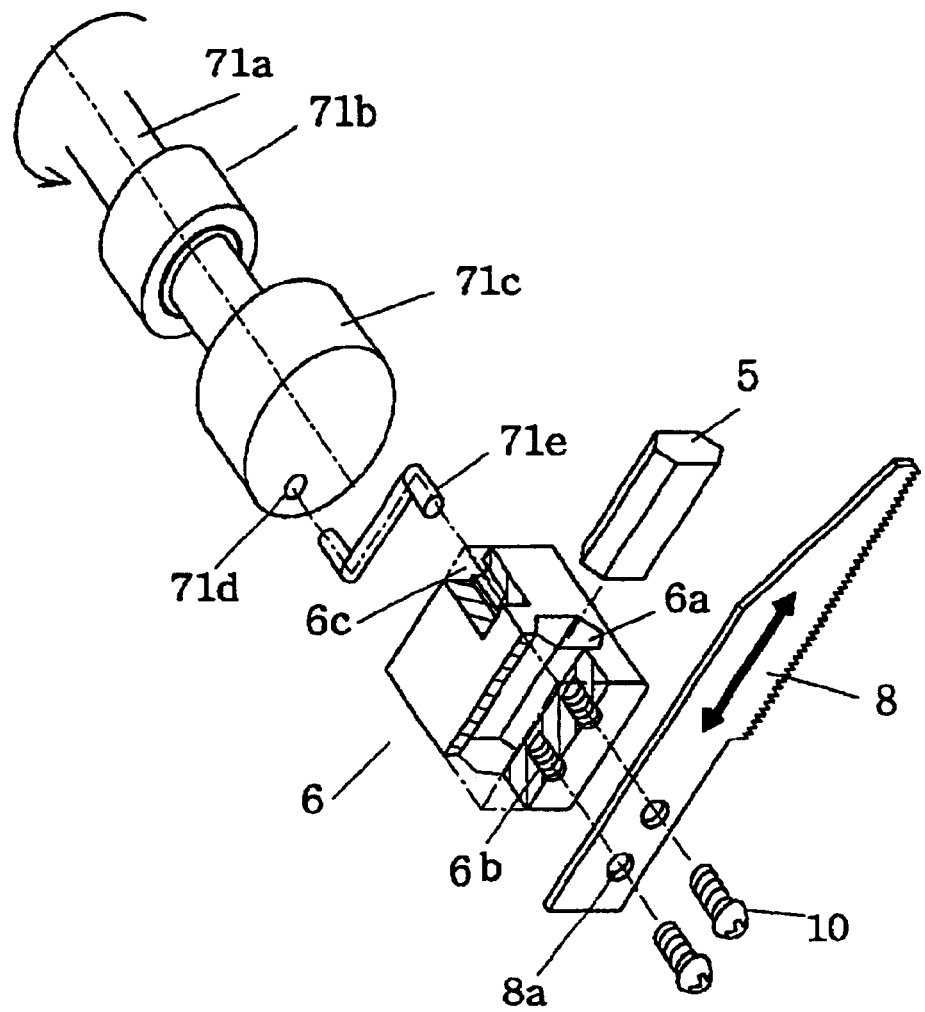
FIG. 3 is an exploded perspective view of a slider coupling portion for the saw blade according to the present invention.

Referring to FIGS. 1 through 3, a reciprocating saw of the present invention includes a handle 1, a neck 2 which is extended from the handle 1, and a head case 3 coupled to the other end of neck 2. In detail, handle 1 includes in the case of the handle 1, a motor 4, and head case 3 includes a slider shaft 5 which forms an angle of approximately 90° with respect to longitudinal direction of the neck 2. Slider 6 is mounted on slider shaft 5, and saw blade 8 is mounted to slider 6 to perform a linear reciprocating cutting motion along the slider shaft 5. Slider 6 and motor 4 are connected by a power linkage device 7 for converting the rotating power of motor 4 into a linear reciprocating cutting motion of slider 6 and transmitting the converted motion to a saw 8 or a file 9 attached to the slider 6, which performs a liner reciprocating cutting motion.

Handle 1 is preferably shaped as a cylinder to which the force of an operator is applied when a bone cutting operation is performed. Handle 1 includes in the cylinder case of handle 1 a motor 4, and outside thereof a switch 1a which turns on/off the motor 4 so as to control the cutting operation of the reciprocating saw.

Neck 2 connects the head case 3 with the handle 1, and is extended from the handle 1 in such a manner that the size of neck 2 is minimized to facilitate the movement of the reciprocating saw in the cutting operation when the saw is deeply inserted into an oral cavity. Components of power linkage device 7 are arranged in the neck 2.

Figure 4:
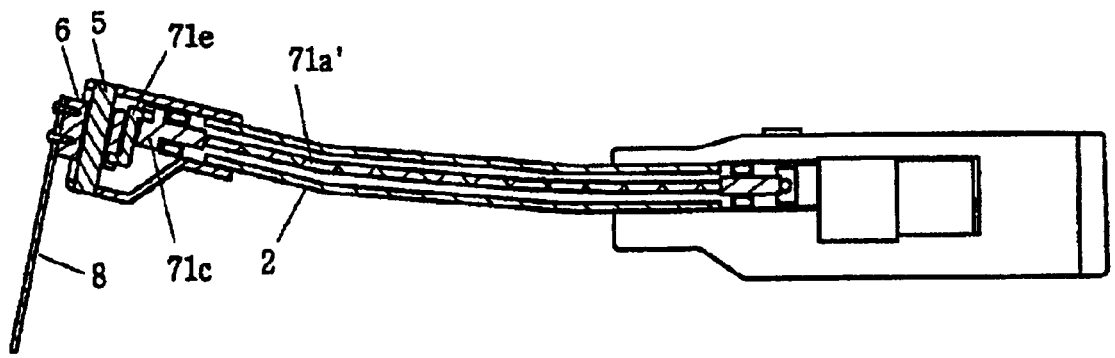
FIG. 4 is a side sectional view of a modified configuration of a reciprocating saw shown in FIG. 1.

Neck 2 may be formed in a straight linear type, or in a bent type if necessary, as shown in FIG. 4. In a bent type neck, it is possible to adjust a proceeding direction (approach direction) of the neck and a linear movement direction (bone cutting direction) of the saw blade by the bent angle of the neck.

Head case 3 provides a movement space for slider 6, and is structured to have a minimum size within a scope of allowing a minimum stroke distance of the saw, so that a smooth operation of the saw can be achieved when the saw is inserted into an oral cavity.

When the range of the stroke pitch distance is 2.5 mm to 3 mm (which is the same as the stroke pitch distance of the slider; designated as "L" in FIG. 1), the head case has a width of approximately 5 mm and a length of approximately 12 mm, thus ensuring a greater movement space for the slider to maximize the stroke pitch distance of the saw. Furthermore, free control of the bone cutting directions and angles can be achieved.

Referring to FIG. 3, slider shaft 5 is installed in the head case 3 in order to induce a linear movement of slider 6. Here, the slider shaft 5 is preferably shaped as a hexagon so as not to be warped during a linear reciprocating movement of slider 6. When the neck 2 is a straight line type, the slider shaft 5 may have a variation of approximately 90° with respect to the neck 2, to thereby achieve a variety of bone cutting directions in conformity with the shapes of cutting portions of the bones.

The above-mentioned hexagonal shape of the slider shaft is for preventing a warpage during slider movements, and can be preferably formed as a cylindrical shaft as shown in FIG. 2b, wherein two slider axes may be arranged in parallel to each other so as to prevent warpage.

Slider 6 performs a linear reciprocating movement along the slider shaft 5 within the head case 3, and has preferably a hexagonal perforation 6a penetrating through a body of slider 6. Slider shaft 5 is assembled into the perforation 6a.

At an outer surface of slider 6, at least one screw hole 6b is formed for a replacement mounting of a saw blade or a file.

Figure 5:
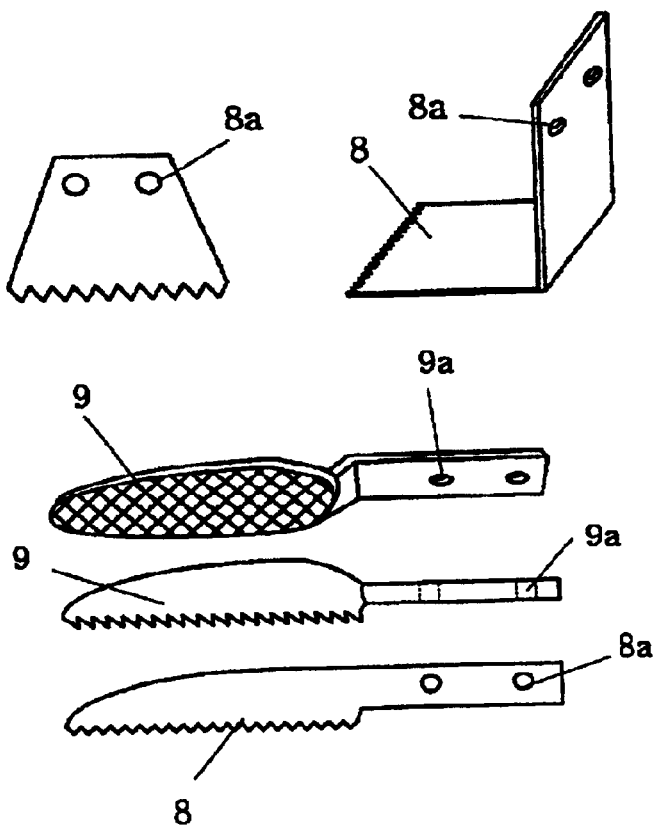
FIG. 5 illustrates several types of saw blades and files for use with the present invention.

Saw blade 8 or file 9 serves to cut a bone, and has at an end portion thereof at least one coupling hole 8a or 9a so as to be coupled to the slider 6 using at least one screw 10, as seen in FIG. 5, which illustrates saw blades 8 and files 9, both of which can have various shapes if necessary.

In the present invention, various embodiments are possible according to the configurations of power linkage device 7 for converting rotation power to a linear reciprocating movement of slider 6 and transmitting the converted movement. Power linkage device 7, as shown in FIGS. 1 through 3, converts the rotating movement of motor 4 to a reciprocating movement of slider 6 using a linkage shaft 71a. Here, linkage shaft 71a is inserted into the neck 2, so that both ends of linkage shaft 71a can be supported by bearings 71b. At such a state, one end of linkage shaft 71a is directly coupled to the motor 4 while the other end of linkage shaft 71a has an expanded member 71c at which an eccentric groove 71d is formed. Slider 6 also has an eccentric groove 6c, and both bent ends of a pin 71e are inserted into the eccentric grooves 71d and 6c, respectively.

In the thus-structured power linkage device, rotating movement of motor 4 is transmitted to linkage shaft 71a, thus providing pin 71e with an eccentric movement at an end of linkage shaft 71a. Then, slider 6 to which the eccentric movement of pin 71e is transmitted slides along slider shaft 5 and thus moves in linear reciprocation perpendicular to linkage shaft 71a. Such a linear reciprocating movement of slider 6 is transmitted to the file or saw blade attached thereto, to thereby perform a bone cutting operation.

Such a power linkage device has a simplified structure, providing conversion of rotating movement of motor into a linear reciprocating movement, and thus minimization of neck size.

As shown in FIG. 4, a linkage shaft may be formed in a flexible cable shaft 71a', so that rotation thereof is enabled even when the neck portion is bent by a predetermined angle. This allows diversity of angles in approach directions and bone cutting directions.

Figure 6:
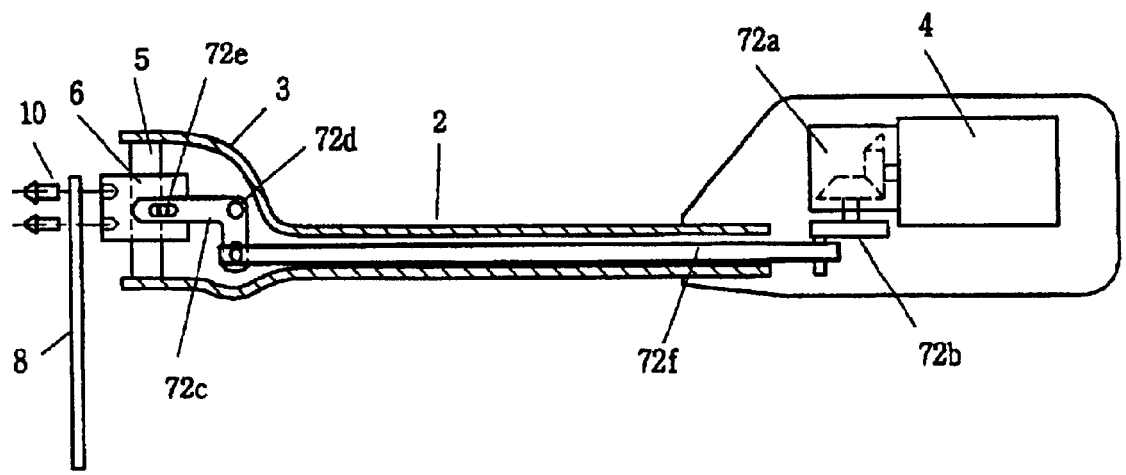
FIG. 6 is a side sectional view of another preferred embodiment of a reciprocating saw according to the present invention.

The power linkage device shown in FIG. 6 has another preferred structure in that the handle portion converts rotation movement of motor 4 to a linear reciprocating movement at the slider using a link node.

That is, a gear element 72a connected to a rotation shaft of motor 4 converts the direction of rotating movement of motor 4 into a right angle. Then, an eccentric wheel shaft 72b is coupled to an end of gear element 72a. L-shaped link 72c is employed inside of head case 3, so that the arrest point of link 72c can be fixed to head case 3 by a hinge 72d and the upper end of link 72c can be coupled to the slider 6 by a hinge 72e. The lower end of link 72c is connected to the eccentric wheel by a rod 72f.

In the above-described configuration, the eccentric wheel shaft 72b is rotated in accordance with the rotation of motor 4, and the rod 72f connected thereto performs crank movements back and forth. Then, the crank movement is transmitted to a linear reciprocating movement by link 72c, thereby linearly reciprocating slider 6.

The above-described configuration is advantageous in that a gear element which is required for changing the direction of power is provided to a handle portion which is not directly related to a bone cutting operation. In addition, internal components of the head case to be directly inserted into bone cutting portion is formed of a thin plate, to thereby minimize the sizes of the head case and handle portion.

Figure 7:
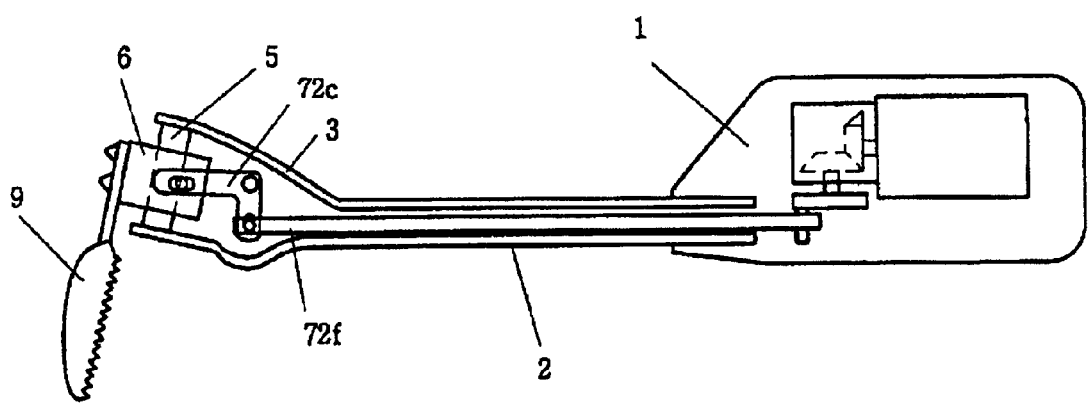
FIG. 7 is a side sectional view of a modified configuration of the reciprocating saw shown in FIG. 6.

FIG. 7 illustrates a modified configuration of the embodiment shown in FIG. 6 where slider shaft 5 is slanted with respect to neck 2. Here, a bone cutting direction is varied by an angle of approximately 90° with respect to the approach direction, and the angle of 90° may be reduced if necessary. Such a configuration may be applied regardless of the configuration of a power linkage device, and is effective for cutting a bone in a narrow portion.

Figure 8A:
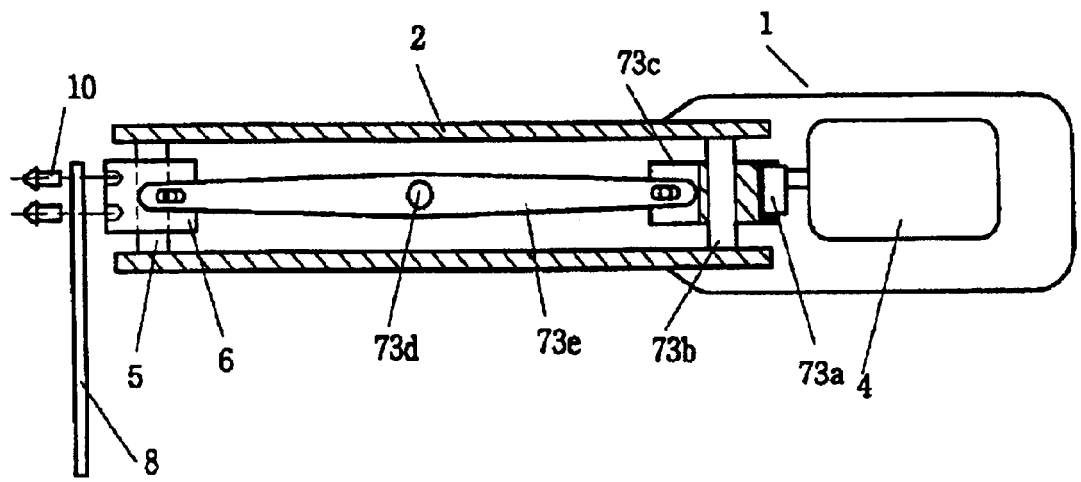
FIGS. 8a and 8b are sectional views of another preferred embodiment of the present invention.

FIG. 8a illustrates another preferred configuration of a power linkage device for converting a rotation movement of the motor into a straight linear movement using a lever 73e moving from right and left in the drawing. An eccentric wheel 73a is coupled to an end of motor 4, and a second slider 73c which performs a straight linear reciprocating movement along a slider shaft 73b is arranged inside of handle 1 and connected to eccentric wheel 73a. Slider 6 and second slider 73c are connected by a lever 73e having at a center thereof a rotation shaft 73d.

Figure 8B:
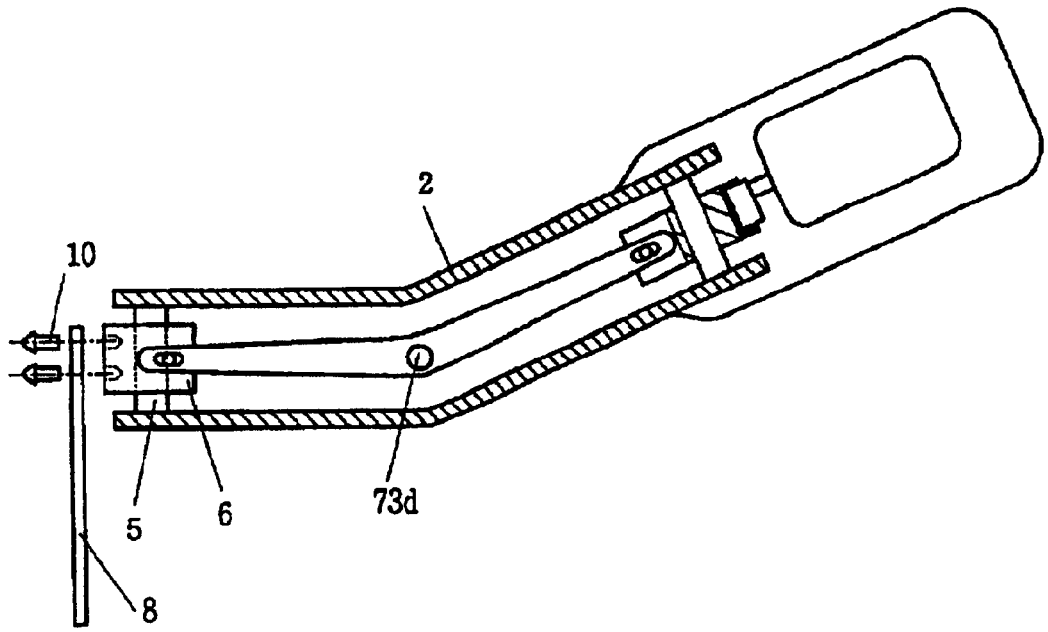

The modified configuration of the embodiment as shown in FIG. 8b is also possible, wherein the power linkage device is bent at a center thereof focused in rotation shaft 73d.

In such a configuration, the eccentric wheel and the second slider constitute a cam element so that the rotating movement of the eccentric wheel can be directly converted into a straight linear reciprocating movement of the second slider. In addition, the slider which constitutes a saw blade operation portion is provided with a straight linear reciprocating movement by the lever which performs an angular movement being centered at rotation axis 73d.

The above-described configuration is minimally disadvantageous in that a neck portion thereof becomes more or less larger since displacement at both ends of the lever becomes larger. However, the head case is formed integrally with the neck portion so as to allow a more smooth operation, and the width of the neck portion is increased in accordance with the displacement of lever being centered at the rotation axis which has least displacement, to thereby provide a wide field of view when the operation is performed.

Figure 9:
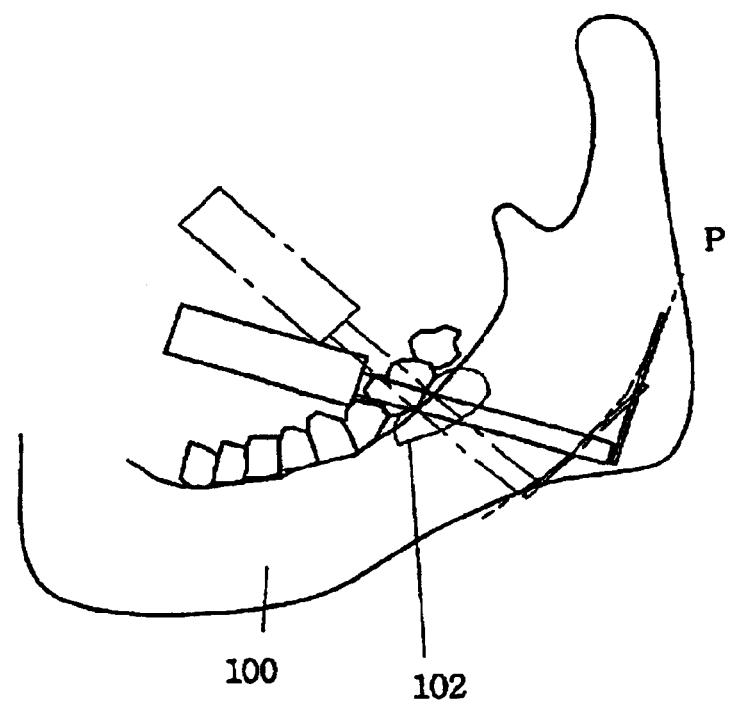
FIG. 9 is a side elevational view showing the reciprocating saw when the reciprocating saw of the present invention is in use.
Figure 10:
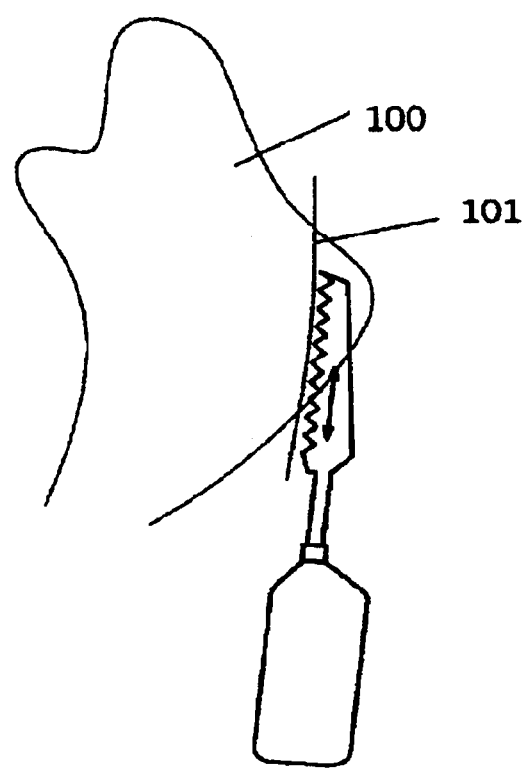
FIGS. 10, 11a, and 11b illustrate configurations and use states of a conventional sagittal saw and a conventional oscillating saw.
Figure 11A:
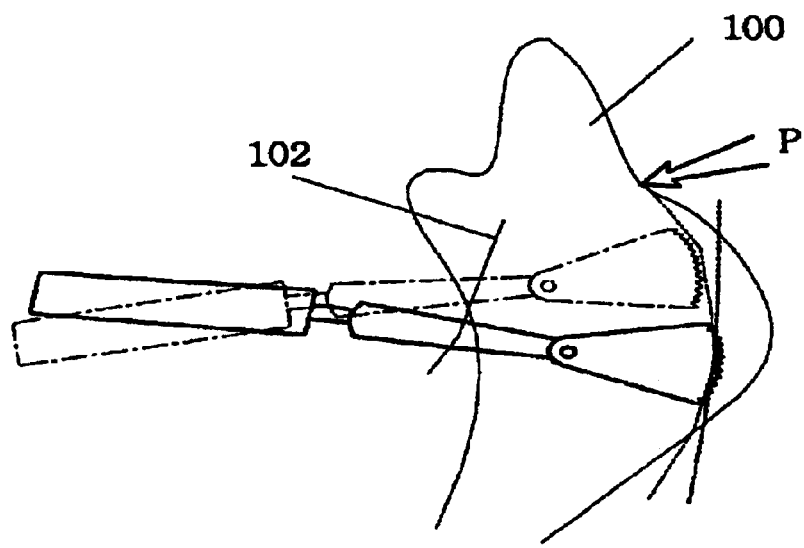
Figure 11B:
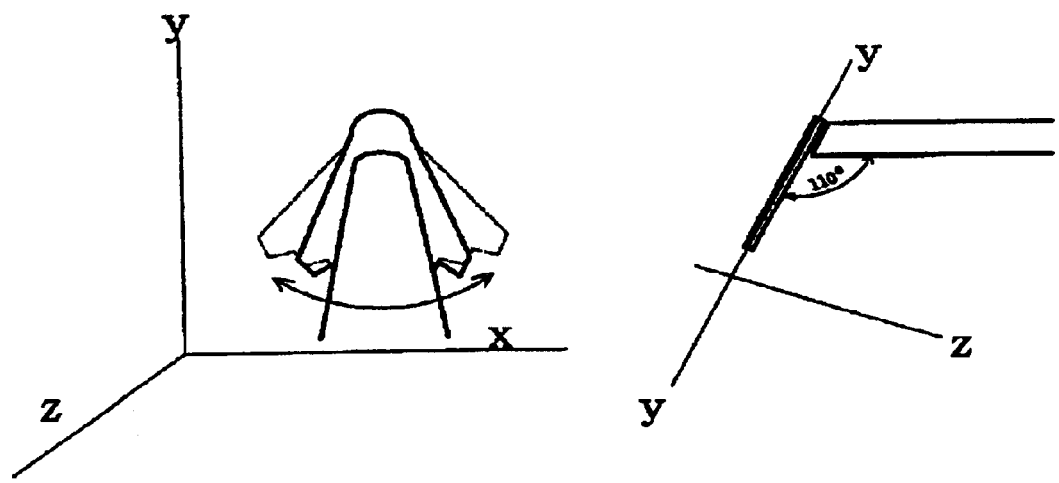

FIG. 9 illustrates a state of cutting the protrusion of a mandible into a circular shape using the reciprocating saw of the present invention. Here, oral cavity cutoff portion 102 is cut off first, and the saw blade is inserted thereinto. Then, the direction of the handle is appropriately adjusted in order to perform a cutting operation.

The direction of bone cutting to be performed by the saw blade is adjusted by means of appropriately adjusting the handle, and the direction of bone cutting forms an approximately 90° angle with respect to the approach direction of the handle. Therefore, free change in direction being centered from oral cavity cutoff portion 102 as an axis is allowed, so that a desired cutoff operation can be rapidly performed.

Specifically, an approach to an upper cutoff portion which was difficult to be performed with a conventional oscillating saw can be easily performed.

In the present invention, direction of the handle and saw blade can be varied within a scope of approximately 90°, so that the cutoff surface and angle of the handle can be suitably adjusted in accordance with a change in angle of the saw blade.

The present invention is advantageous in that the size of the saw blade operation portion is minimized to allow free operation and a wide field of view in a narrow space of the oral cavity, the rotation power generated at the handle can be converted into a straight linear reciprocating movement of the saw blade operation portion, and the direction of cutting a bone has an angle of approximately 90° with respect to the approach direction. Thus, a significantly high efficiency in a bone cutting operation can be achieved since the bone cutting operation is performed by the linear reciprocating movements. In contrast to a conventional sagittal type saw, the reciprocating saw of the present invention allows a smooth operation even in a narrow space, ensuring a wide field of view. The bone cutting surgery can be performed only by partially cutting the oral cavity. In addition, a portion such as an upper cutoff portion of a mandible to which a conventional saw has difficulty in approaching, can be easily approached and cutoff performed with the present invention.

A saw or file of the present invention can be replaced by each other. Therefore, it is possible to rapidly replace a saw or a file with each other in accordance with the shapes of the cutoff portion.

While the invention has been particularly shown and described with reference to preferred embodiments thereof, it will be understood by those skilled in the art that various changes in form and details may be made therein without departing from the spirit and scope of the invention.

What is the claimed is:

1. A reciprocating surgical tool for use in an oral cavity operation, comprising a handle, a neck extending from said handle at a first end, and a head case coupled to a second end of said neck; a motor mounted inside of said handle; a slider shaft mounted inside of said head case having an angle of approximately 90° with respect to a longitudinal axis of said neck; a slider movable in a linear reciprocating direction along said slider shaft; a tool member mounted to said slider for performing said oral cavity operation; and a power linkage device coupled between said slider and said motor for converting rotation power of said motor into linear reciprocating movement of said slider, whereby a direction of the oral cavity operation performed by said tool member mounted to said slider forms an angle of approximately 90° with respect to the longitudinal axis of the neck.

2. A reciprocating surgical tool according to claim 1, wherein said power linkage device comprises a linkage shaft inserted into said neck, such that both ends of said linkage shaft are supported by a bearing, one end of said linkage shaft being directly coupled to said motor while the other end of said linkage shaft has an expanded member at which an eccentric groove is formed, and a pin, a first bent end of the pin being inserted into said eccentric groove of said expanded member and a second bent end of the pin being inserted into an eccentric groove of said slider, respectively.

3. A reciprocating surgical tool according to claim 1, wherein said power linkage device comprises a gear element connected to a rotation shaft of said motor so as to convert the direction of rotation movement of said motor into a right angle; an eccentric wheel shaft coupled to an end of said gear element; and an L-shaped link located within said head case, such that an arrest point of said L-shaped link is fixed to said head case by a first hinge, an upper end of said L-shaped link being coupled to said slider by a second hinge, and a lower end of said L-shape link being connected to an eccentric wheel by a rod.

4. A reciprocating surgical tool according to claim 1, wherein said power linkage device comprises an eccentric wheel coupled to an end of said motor, and a second slider for linear reciprocating movement along a slider shaft being position within said handle for coupling to said eccentric wheel; and wherein said slider and second slider are connected by a lever having at a center thereof a rotation shaft.

5. A reciprocating saw for use in an oral cavity bone cutting operation, comprising:
   a handle;
   a motor;
   a linkage for converting rotating power of said motor into linear reciprocating movement;
   a slider shaft mounted at an end of said linkage having an angle of approximately 90° with respect to the linkage; and
   a slider, for attaching one of a saw and a file, which moves reciprocatingly along said slider shaft, whereby a direction of a bone cutting operation performed by the saw or file attached to said slider forms an angle of approximately 90° with respect to a longitudinal axis of said handle.

6. A reciprocating saw according to claim 5, further comprising a switch for turning on/off the motor.

7. A reciprocating saw according to claim 5, wherein said linkage includes:
   a linkage shaft connected between the motor and the slider for transmitting the rotating power from the motor to the slider;
   the slider having at least one eccentric groove; and
   a pin having a pair of bent ends, such that one bent end is inserted into the eccentric groove of the slider while the other end is inserted into an eccentric groove of the linkage shaft, whereby the rotating power of the motor is converted into linear reciprocating movement of slider.

8. A reciprocating saw according to claim 7, further comprising at least one bearing to support the linkage shaft.

9. A reciprocating saw according to claim 7, wherein the linkage has a curved shape for adjusting a working direction and bone cutting direction.

10. A reciprocating saw according to claim 5, wherein the linkage includes:
    a gear element consisting of two gears perpendicularly engaged with each other, one of which is connected to a rotation shaft of said motor and the other of which connected to an eccentric wheel shaft, in order to convert a direction of rotation movement of said motor into a right angle;
    the eccentric wheel shaft being connected to a rod so that the rotating power of the gear is transferred to the rod;
    the rod being connected to a lower portion of an L-shaped link so that the reciprocating movement of the rod is transmitted to the lower portion of the L-shape link; and
    an upper portion of the L-shaped link being connected to the slider such that it pivotably moves up and down along the slider by transmitted movements of the rod through a hinge, whereby the rotating power of the motor is converted into a linear reciprocating movement of slider.

11. A reciprocating saw according to claim 10, wherein the L-shape link is installed in a head case at an end of the linkage opposite said handle.

12. A reciprocating saw according to claim 5, wherein said linkage includes:
    a eccentric wheel coupled to an end of the motor; and
    a second slider connected to the eccentric wheel and for reciprocating movement along the slider shaft; wherein the slider is connected to the second slider by a lever having at a center thereof a rotation shaft.

13. A reciprocating saw according to claim 12, wherein the lever has a bent shape.

* * * * *